US010485427B2

(12) United States Patent
Demos

(10) Patent No.: US 10,485,427 B2
(45) Date of Patent: Nov. 26, 2019

(54) SYSTEM AND METHOD FOR SYNTHESIS OF IMPEDANCE MATCHING AND SIGNAL CONVERTING MATERIAL FOR ALL OPTICAL PHOTO-ACOUSTIC DETECTION

(71) Applicant: Lawrence Livermore National Security, LLC, Livermore, CA (US)

(72) Inventor: Stavros Demos, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 297 days.

(21) Appl. No.: 14/534,471

(22) Filed: Nov. 6, 2014

(65) Prior Publication Data

US 2016/0128578 A1 May 12, 2016

(51) Int. Cl.
*A61B 5/00* (2006.01)
*A61K 49/22* (2006.01)
*A61K 49/00* (2006.01)

(52) U.S. Cl.
CPC .......... *A61B 5/0095* (2013.01); *A61B 5/4064* (2013.01); *A61B 5/4076* (2013.01); *A61K 49/0006* (2013.01); *A61K 49/226* (2013.01)

(58) Field of Classification Search
None
See application file for complete search history.

(56) References Cited

U.S. PATENT DOCUMENTS

2003/0233045 A1* 12/2003 Vaezy ................. A61B 8/4281
600/437
2007/0187632 A1* 8/2007 Igarashi ............... A61B 5/0048
250/559.36
(Continued)

OTHER PUBLICATIONS

Wikipedia contributors. Gel. Wikipedia, The Free Encyclopedia. May 5, 2017, 21:47 UTC. Available at: https://en.wikipedia.org/w/index.php?title=Gel&oldid=778904704. Accessed May 26, 2017.*
(Continued)

*Primary Examiner* — Katherine L Fernandez
(74) *Attorney, Agent, or Firm* — Harness, Dickey & Pierce, PLC

(57) ABSTRACT

A system and method is disclosed for non-contact detection and/or imaging and/or monitoring target subsurface tissue of at least one of human or animal anatomy. The system applies a first optical excitation signal to an outer tissue surface at a first location on the anatomy, which excites the target subsurface tissue to produce acoustic signals which are transmitted to an outer tissue surface of the anatomy. A gel-like, impedance matching and signal converting (IMASC) material layer is applied to the outer tissue surface at a second location on the anatomy. The IMASC material layer contains material elements which are able to influence characteristics of an optical signal impinging and reflected from the IMASC material, in accordance with acoustic signals that have been reflected from the target subsurface tissue, and which propagate into the IMASC material. An optical ultrasound detection system is used to process the reflected optical signals reflected from the IMASC material to provide information that may be used to provide an image of the target subsurface tissue.

12 Claims, 3 Drawing Sheets

(56) References Cited

U.S. PATENT DOCUMENTS

| | | | |
|---|---|---|---|
| 2009/0002685 A1* | 1/2009 | Fukutani | A61B 5/0073 356/72 |
| 2009/0221919 A1* | 9/2009 | Ben Dor | A61B 5/0059 600/473 |
| 2010/0222658 A1* | 9/2010 | Cheng | A61B 5/14553 600/324 |
| 2013/0338504 A1* | 12/2013 | Demos | A61B 5/0097 600/443 |

OTHER PUBLICATIONS http://nanocomposix.com/products/50-nm-econix-silver-nanospheres, at least one day prior to Nov. 6, 2014, 5 pp.

http://nanocomposix.com/products/15-nm-econix-gold-nanospheres, at least one day prior to Nov. 6, 2014, 4 pp.

http://nanocomposix.com/pages/nanoparticles-by-material, at least one day prior to Nov. 6, 2014, 3 pp.

http://nanocomposix.com/collections/silver, at least one day prior to Nov. 6, 2014, 20 pp.

http://nanocomposix.com/collections/gold, at least one day prior to Nov. 6, 2014, 8 pp.

http://nanocomposix.com/collections/silica, at least one day prior to Nov. 6, 2014, 3 pp.

http://nanocomposix.com/collections/platinum-nanoparticles, at least one day prior to Nov. 6, 2014, 3 pp.

http://nanocomposix.com/collections/titanium-dioxide-nanoparticles, at least one day prior to Nov. 6, 2014, 7 pp.

http://nanocomposix.com/products/20-nm-magnetite-nanoparticles, at least one day prior to Nov. 6, 2014, 7 pp.

http://nanocomposix.com/collections/copper-oxide-nanoparticles, at least one day prior to Nov. 6, 2014, 3 pp.

http://nanocomposix.com/collections/magnetic-nanoparticles, at least one day prior to Nov. 6, 2014, 6 pp.

http://www.sonicator.com/nanoparticle-dispersion.shtml, at least one day prior to Nov. 6, 2014, 4 pp.

http://www.silversolutionusa.com/silver-sol-8-ounce-10 ppm, at least one day prior to Nov. 6, 2014, 5 pp.

\* cited by examiner

SYSTEM AND METHOD FOR SYNTHESIS OF IMPEDANCE MATCHING AND SIGNAL CONVERTING MATERIAL FOR ALL OPTICAL PHOTO-ACOUSTIC DETECTION

FIELD

The present disclosure relates generally to optical imaging systems, and more particularly to a non-contact, optical imaging system which is well suited for imaging subsurface human or animal tissue.

BACKGROUND

The statements in this section merely provide background information related to the present disclosure and may not constitute prior art.

Traumatic Brain Injury (TBI) is the leading cause of death for people under the age of 45. Approximately five million Americans currently suffer some form of TBI disability. More than 90% of TBIs are the result of the brain shearing against the inside of the skull after an acute event. The Defense and Veterans and Brain Injury Center states: "Traumatic brain injury (TBI) is a significant health issue which affects service members and veterans during times of both peace and war. The high rate of TBI and blast-related concussion events resulting from current combat operations directly impacts the health and safety of individual service members and subsequently the level of unit readiness and troop retention."

Children, especially newborns, are much more vulnerable to TBI. Head injuries among children account for approximately 100,000 hospitalizations annually. TBI associated with professional or recreational sports activities is also a well recognized problem, with approximately 350,000 sports-related head injuries treated at U.S. hospital emergency rooms every year.

A significant challenge is early detection of TBI injuries and effective monitoring of a patient who is suspected of having suffered a TBI. Early detection and monitoring during the first few hours after a TBI is suspected of having occurred can potentially reduce long term complications for the patient and enable health professionals to more effectively treat the patient.

SUMMARY

The present disclosure relates to a system for non-contact imaging target subsurface tissue of at least one of human or animal anatomy. The system applies a first optical excitation signal to an outer tissue surface at a first location on the anatomy, which excites the target subsurface tissue to produce acoustic signals which are transmitted to an outer tissue surface of the anatomy. A gel-like, impedance matching and signal converting (IMASC) material layer is applied to the outer tissue surface at a second location on the anatomy. The IMASC material layer contains material elements which are able to influence characteristics of an optical signal impinging and reflected from the IMASC material, in accordance with acoustic signals that have been reflected from the target subsurface tissue, and which propagate into the IMASC material. An optical ultrasound detection system is used to process the optical signals reflected from the IMASC material to provide information that may be used to construct an image of the target subsurface tissue.

In another aspect the present disclosure relates to a method for non-contact imaging target subsurface tissue of at least one of human or animal anatomy. The method may comprise applying a gel-like, impedance matching and signal converting (IMASC) material layer to an outer tissue surface at one location on the anatomy. An optical excitation signal may be generated which is applied to the outer tissue surface at another location on the anatomy. The optical excitation signal excites the target subsurface tissue to produce acoustic signals which are transmitted to an outer tissue surface of the anatomy. An optical signal is directed at the gel-like IMASC material. One or more reflected signal portions of the optical signal are received back from the IMASC material, where the reflected signal portions have been modified by the gel-like IMASC material in relation to the acoustic signals generated from the target subsurface structure. The reflected signal portions are used to generate electrical signals which enable an image of the subsurface target tissue to be constructed or the signal to be monitored.

In still another aspect the present disclosure relates to a low viscosity, gel-like impedance matching and signal converting (IMASC) material adapted to be applied to a skin surface, for use with a non-contact imaging system, for imaging and/or detecting and/or monitoring a target subsurface tissue of at least one of human or animal anatomy. The IMASC material may comprise a base gel and nanoparticles dispersed generally uniformly in the base gel. The nanoparticles operate to enable an optical signal directed at the IMASC material to be modified in relation to separate acoustic signals transmitted to the target subsurface tissue and reflected therefrom back to the IMASC material. In this manner the optical signal is influenced by the reflected acoustic signals as the optical signal is reflected by the IMASC material.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
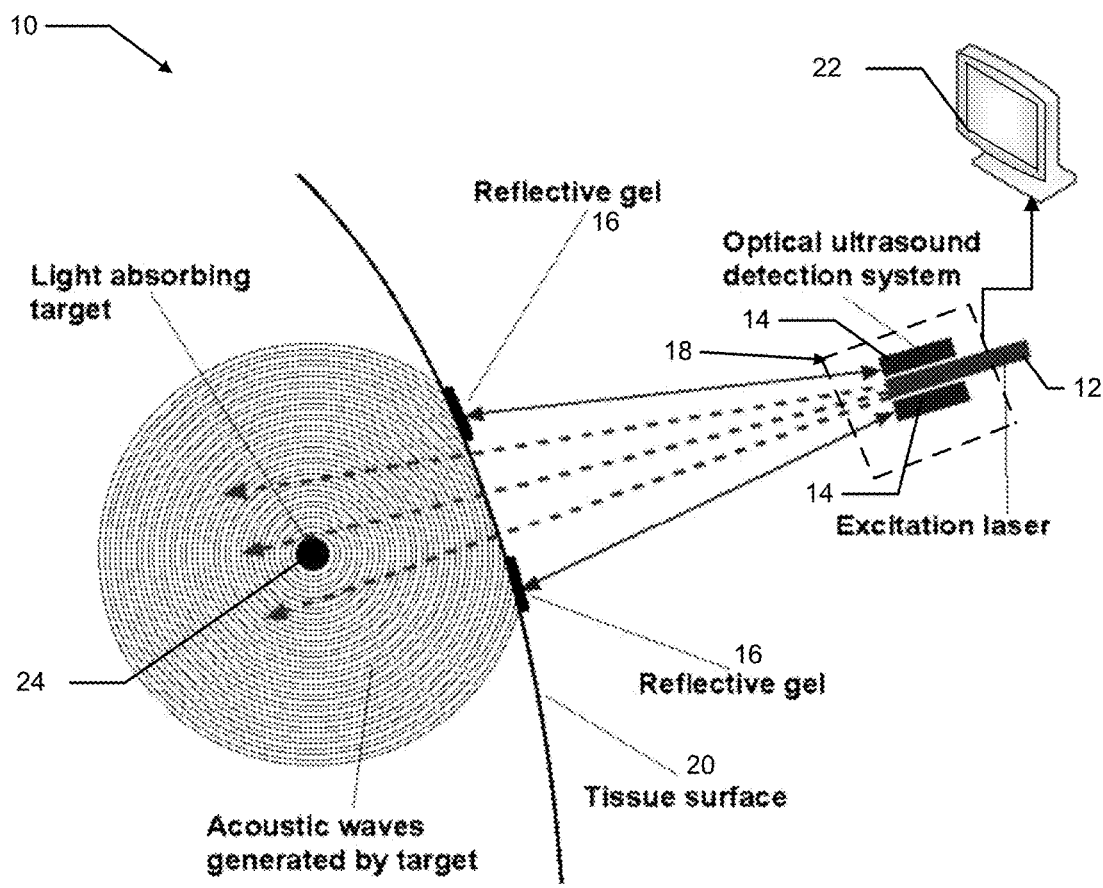
FIG. 1 is a high level block diagram of one embodiment of a system in accordance with the present disclosure.

The following description is merely exemplary in nature and is not intended to limit the present disclosure, application, or uses. It should be understood that throughout the drawings, corresponding reference numerals indicate like or corresponding parts and features.

The present disclosure relates to a new technology that is particularly well suited to address early detection and continuous monitoring during the initial critical hours following a TBI event. It is anticipated that this technology will lead to portable, low cost instrumentation that can be deployed in a clinical setting or in the field. The present disclosure involves methods that utilize light to generate acoustic waves inside the body. The acoustic waves are subsequently detected via a non-contact optical method to generate an image (or information) that is similar to what can be obtained with conventional photo-acoustic imaging. This image contains morphological and functional information that may capture evidence indicating an initial stage of a TBI, and well as the development of a TBI.

The present disclosure is based on the non-contact detection of acoustic waves following the injection of light pulses into the tissue. The light pulses may be in the range of about 5 ns-10 ns, but may also be longer in duration, such as up to about 100 ms. This light is preferentially absorbed by structures of interest within the skull such as an abnormal blood concentration associated with TBI hematomas in the brain. The resulting pressure waves (produced by the heating and subsequent relaxation of the light absorbing regions) allow detection and/or imaging of the light-absorbing tissue structures within the skull in a way similar to that of conventional ultrasound devices. In conventional ultrasound imaging the original acoustic waves are injected into the tissue by the ultrasound device, and imaging is based on detecting the signal reflected back to the device by tissue structures. The present disclosure, however, uses the tissue structures of interest as the primary generators of the acoustic signal. Furthermore, one or more optical wavelengths can be used for excitation. The resulting image contrast (quantified by the generated acoustic signal strength) induced by each distinct wavelength is determined by the corresponding molar absorptivity of the targeted light-absorbing biological molecules (such as hemoglobin).

For the example of a TBI, the state and treatment of a hematoma is based both on anatomical and functional information. Although the size and location of anatomy affected by a TBI can be currently obtained with a CT scan, the proposed methods disclosed herein can, in addition, provide highly important, functional information. Specifically, factors of significant clinical importance with a TBI are believed to be the hemoglobin oxygenation (relative concentration of oxyhemoglobin and deoxyhemoglobin), and in the case of hematomas, the methemoglobin saturation. With the proposed methods of the present disclosure, the signal generated using excitation at multiple optical wavelengths can provide information on the state of the blood (a method similar to pulse oximetry), thus obtaining functional information that currently cannot be directly measured. This method also can be used for continuous monitoring as there is no exposure to ionizing radiation or any other potentially harmful form of energy or radiation.

The above-provided short overview of the technology that the present disclosure involves highlights three technology elements involved in implementing a system in accordance with the present disclosure: 1) the use of light pulses of highly controlled duration and wavelength to generate acoustic waves; 2) the acquiring and use of the resulting acoustic waves originating from an object, in response to being irradiated with the light pulses, to generate an image; and 3) the non-contact detection of the acoustic waves for the purpose of generating an image.

The present disclosure makes use of these three technical elements, and particularly the non-contact detection of the acoustic waves, to enable a system and method to be created which is expected to revolutionize and expand on the general use of light pulses and acoustic waves for imaging purposes. The present disclosure leverages the combination of these three technological elements to create a new non-contact imaging system and method which is well suited for both medical and non-medical applications, but is especially well suited for the detection and monitoring of TBI events.

The detection of ultrasound waves with optical techniques (also referred to as laser-ultrasonics) is a well-established technique that is used for non-contact generation and detection of ultrasound in industrial materials such as metals, plastics, and polymer-matrix composites. Direct application of this technique was recently demonstrated in tissues using the reflection from the surface of specially prepared, partially dehydrated slices of homogeneous animal tissue. However, the authors stated that the reflected signal was very weak and required high laser intensities that made this approach impractical in a clinical setting. From a practical standpoint, it is virtually impossible to apply this same method clinically because of several reasons. For one, light reflection from the skin is diffusive and the signals from different points interfere to generate a strong background speckle noise. The tissue surface is also unpredictably not-flat, thus degrading the signal information. Lastly, the highly variable hydration of human skin affects its reflectivity and therefore limits signal quantification. The novel approach entailed with the present disclosure addresses these issues and in addition, significantly increases the sensitivity for detection of acoustic waves.

The present disclosure is based in part on the localized application of a gel-type material that is specifically designed to optimize conversion of the acoustic signal to an optical signal. Ultrasound waves are typically strongly reflected by a surface or object that presents impedance mismatching (such as at the skin-air interface). For this reason, an impedance matching, low viscosity material, such as oil-like, cream-like or gel-like material, is typically used to achieve coupling of the ultrasound wave energy to the detection system. The approach of the present disclosure is based in part on the conversion of the vibrational signal carried by the pressure, acoustic or ultrasound wave into an optical signal via the use of a specially designed low viscosity, gel-type, impedance matching and signal converting ("IMASC") material (hereinafter sometimes referred to simply as "gel-type IMASC material") that is applied on the surface of the skin. For the following discussion, it will be understood that the terms "low viscosity" and "gel-type" may be used interchangeably, and refer to a material having a relatively low viscosity which imparts to it a cream-like or gel-like consistency or quality. This gel-type, impedance matching material is designed to offer two functions. The first is to provide impedance matching with the tissue so that the ultrasound waves can effectively propagate into the gel-type impedance matching material. The second function is to help the ultrasound waves to better interact with custom optical elements of microscopic size that are embedded in the gel-type impedance matching material in a fashion that enables the gel-type material to use the ultrasound waves (i.e., acoustic signals) to help modify an optical signal that enters the gel-type material, and to therefore impart the information represented by the acoustic signals into a corresponding optical signal. This may be achieved by the microscopic optical elements functioning as various types of mechanisms to help cause modulation of the optical intensity, phase, polarization, complex index of refraction, or to influence other types of optical properties of an optical signal that is directed into the gel-type material from an external light source. In this way the interaction of the microscopic optical elements with the ultrasound waves can be used to convert the information in the vibration signals (i.e., impart the vibrational information from the acoustic signals) into an optical signal that is impinging the gel-type material.

FIG. 1 depicts one example of a system 10 in accordance with the present disclosure. The system 10 in this example may make use of at least one light source, but in this example two different light sources 12 and 14 are shown, along with a gel-type IMASC material 16. Light source 12 is an optical excitation light generating system (ELS) and may comprise a pulsed light source, for example a pulsed laser that may be also equipped with an optical parametric oscillator module (hereinafter referred to interchangeably either as "ELS laser 12" or as "optical excitation signal generating system 12"), and is used to provide optical excitation energy. The wavelength of the ELS laser 12 may be tuned to obtain functional information as discussed earlier. The functional information that can be obtained is related to the physiological state of hematoma lesion such as epidural hematoma or subdural hematoma due to an injury. It is known that the optical absorption properties of the hemoglobin in the blood change depend on the state of the hemoglobin. Specifically, while the common normal states of hemoglobin are the oxyhemoglobin and the deoxygenated hemoglobin (which are related to oxygen saturation), hemoglobin can also transform to methemoglobin (which relates to the oxidation state of the ligand iron ion) and other forms. Typically these different forms of the basic hemoglobin molecule found in blood exhibit differences in their optical absorption spectra (which represent the strength of the absorption as a function of wavelength). The method discussed in this invention takes advantage of these differences by using more than one (that is, multiple) appropriately selected ELS wavelengths and determining the strength of the detected acoustic signal transported through the gel-like IMASC material 16. The relative difference of the signal generated at different wavelengths provides direct information on the state of the hemoglobin in the target area. In turn, this information can be used to assess and monitor the progress of the hematoma lesion, such as if there is blood flow within the lesion, the oxygenation level, the amount of methemoglobin (typically signifying that there is no or reduced blood circulation). The strength of the signal at each wavelength as a function of time can provide additional information regarding the physiological condition of the target lesion. The second light source 14 is part of the optical ultrasound detection system 18 and is used to illuminate one, two, or potentially more than two, other spaced apart locations on an outer tissue surface 20 where the gel-type IMASC material 16 has been applied. The vibrations of the outer tissue surface 20 occurring as a result of acoustic signals generated by the subsurface target tissue 24, as a result of being irradiated by the excitation signal from the ELS laser 12, may be used by the gel-type IMASC material 16 to help create optical signals that include information pertaining to the imaged subsurface target tissue 24. These converted acoustic-to-optical signals, caused in part by the gel-type IMASC material 16, may be detected by the optical ultrasound detection system 18.

It will be appreciated that images would require scanning point by point the ELS laser 12 over the tissue area of interest to obtain an acoustic signal from each location, and the detected signal from each location can be converted to an image of the area. Alternatively, the ELS laser 12 may be positioned in a fixed location and monitor the changes in this location with time (i.e., to obtain a temporal profile of the response). A combination of the above is also possible.

It will also be appreciated that using one IMASC location may be sufficient. Using more than one can enhance the ability to detect the signal, especially if when scanning a large area.

Another important advantage is that with the method presented of the present disclosure, the entire spectrum of acoustic waves generated can be detected with no loss in sensitivity with wavelength compared to the narrow spectral range using conventional ultrasound detectors. The key is that low frequencies travel more efficiently (lower losses) but have lower spatial resolution as well. Here the spatial resolution is not an issue because it is determined (and limited by) the ability of the ELS laser 12 to reach the target lesion. That is, the location of the lesion is known because it is the same as the location of injection of the signal from the ELS laser 12. More than one detection IMASC locations can also be used in order to enhance the ability of the system to more accurately locate the location (including the depth) of the target tissue. Also, the ELS laser 12 may not be a laser but may be some other type of light source. The same goes for the second source that detects the acoustic signal.

Figure 2:
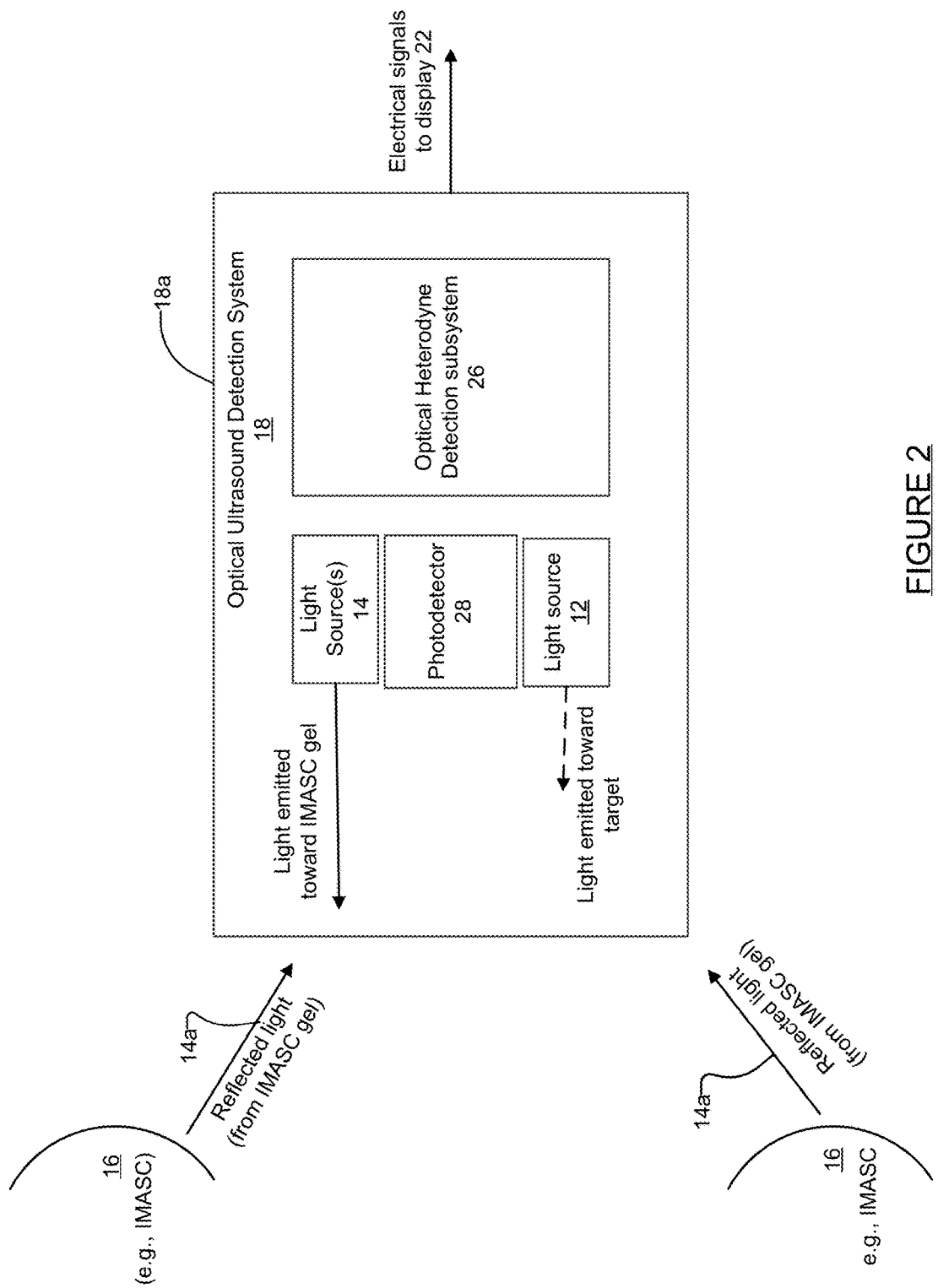
FIG. 2 is a high level block diagram of one example of the components that may make up the optical ultrasound detection system.

With brief reference to FIG. 2, the optical ultrasound detection system 18 is shown in greater detail contained in a housing 18a. Again, this is just one example of a suitable optical detection system, and those skilled in the art will appreciate that the function of this subsystem could be performed by other types of subsystems. The optical ultrasound detection system 18 may incorporate an optical heterodyne detection subsystem 26 such as those widely used for sensing the motion of remote objects. Examples include LIDAR systems for remote sensing of atmospheric pollutants, Doppler velocimetry for measuring speeds of particles entrained in flowing gas streams such as wind tunnels, and tracking of shock fronts in high explosive detonations. In all cases a single-frequency laser beam is first split into two parts: one part is directed and in part specularly reflected by the gel-type IMASC material 16 modulated by the acoustic signals originating from the target tissue 24 (indicated by light rays 14a in FIG. 2), which is combined with a portion of light (not shown) from light source 12 which is reflected from a reference surface (not shown). Analysis of the resulting interference, or beat signal, yields line-of-sight velocities ranging from millimeters to kilometers per second. In addition, the natural gain of the optical heterodyne process and its inherent rejection of contamination by stray light make it an ideal sensing method for ambient light conditions. The analyzed signal that may be used to create an image (or images) on a suitable display 22 or used to generate temporal profiles of the signal or the functional information obtained from the analyzed signals. Display 22 may be a CRT, LCD, OLED, or any other suitable type of display device. It is possible that a desktop computer system, a laptop, a smartphone, or another type of computing device having a suitable display may also be used to receive the electrical signals output from the optical ultrasound detection subsystem 18 (either by a wired connection or a wireless connection). Still further, it is possible for the electrical signals to be transmitted converted into Internet Protocol ("IP") packets and transmitted over a wide area network (e.g., the Internet) to a remotely located computing/display system for display and analysis at a remote location. In any event, the images produced on the display 22 may be used by a medical professional for the non-contact analysis of subsurface tissue.

The optical heterodyne detection subsystem 26 discussed above is based on the coherence property of the detection signal. Alternative methods can be employed to detect either the coherence or other property of the light used by the detection system. For example, the heterodyne detection subsystem 26 can be replaced with a different system that detects changes in the polarization of the detection signal. In this case, the IMASC material is designed to convert the modulation of the acoustic signals into a modulation of the polarization property of the detection signal. Other methods may be based on frequency shift detection or other methods that can be enabled by the specific design of the IMASC material to convert the acoustic (vibrational) signal into an optical signal.

An important feature of the methodology of the present disclosure is that the location of the injection of the excitation light from the ELS laser 12 and the location(s) of detection of the acoustic waves are not the same. This is illustrated in FIG. 1, where it can be seen that the locations where detection takes place, represented by areas of the reflective gel-like IMASC material 16, are laterally offset from where the optical excitation signal from excitation laser 12 is passing through the outer tissue surface 20. This important feature greatly enhances the capabilities of the overall system 10. Specifically, the detection of the same signal at one or more different locations (i.e., different from where the optical excitation signal from ELS laser 12 enters the outer tissue surface 20, and thus, different from where the acoustic signal is generated) enables increased sensitivity and an increased volume of information to be obtained. This significantly helps to improve signal quantification and enables obtaining high quality images from the detected optical signals. Also, the detection of the acoustic waves can be performed in locations where the skull is relatively thin or locations where there is a natural opening in the skull and acoustic wave attenuation is relatively weak. With conventional ultrasound devices, the reflection of the injected acoustic waves by the skull becomes the source of image distortion and artifacts. This severely limits the use of conventional ultrasound systems with head traumas to a very small number of sites, and typically to younger children. On the other hand, light propagation through the skull is less significantly limited by the thickness of the skull. Therefore, the optical excitation signal can be delivered (or scanned) at the area of interest of the head while the detection can be performed in a suitable accessible location that provides increased acoustic signal propagation and/or are outside of areas of the head that cannot be accessed due to the injury.

Figure 3:
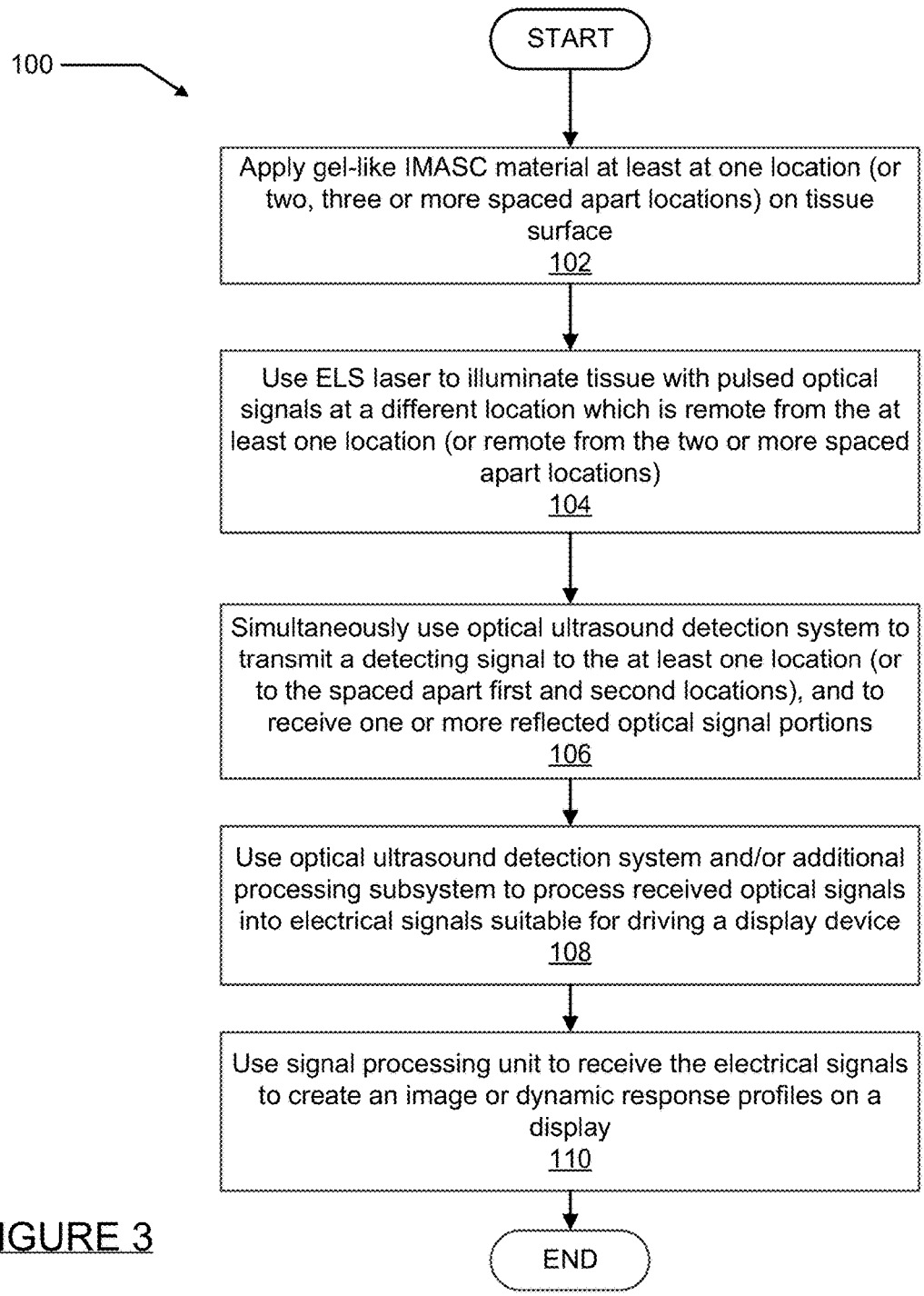
FIG. 3 is a flowchart illustrating a plurality of operations that may be performed by the system of FIG. 1 when performing non-contact imaging of subsurface tissue.

Referring briefly to FIG. 3, a flowchart 100 is shown that illustrates one example of various operations that maybe performed by the system 10 shown in FIG. 1, to implement one example of a methodology in accordance with the present disclosure. The operations of the flowchart 100 will be discussed in connection with an example in which human tissue is imaged, although it will be appreciated that the system 10 is expected to find utility in imaging subsurface anatomy of animals as well.

Initially a reflective gel-type IMASC material (i.e., gel-like IMASC material 16 in FIG. 1) may be applied to one location, or possibly to first and second spaced apart locations of the tissue, or possibly to three or more spaced apart locations, as indicated at operation 102. At operation 104 the ELS laser 12 is used to direct pulsed optical signals at a different location which is remote from the one location (or remote from the two or more spaced apart locations. At operation 106 the optical ultrasound detection system 18 is simultaneously used to transmit a detecting signal to the at least one location (or the two or more spaced apart locations) and to receive one or more reflected signal portions 14*a*. At operation 108 the optical ultrasound detection system 18 may be used to process the reflected optical signal portions generated from the gel-like IMASC material 16 into electrical signals. The electrical signals may then be used by a signal processing unit to create an image (or images) on the display device 22 that relate to the subsurface target tissue 24 (FIG. 1).

There are numerous additional benefits from the technology employed by the system 10 and method of the present disclosure. For one, detection of the entire spectrum of acoustic waves is possible. The bandwidth is typically on the order of 100 MHz while ultrasound transducers are sensitive over only a much narrower frequency range. Another significant benefit is the non-contact detection and continuous monitoring that the system 10 affords. The frequency domain can be used to optimize signal sensitivity for propagation through the skull and/or enable detection using the acoustic signal passing through a natural opening in the skull. Using optical excitation signals at different wavelengths, the present system 10 may be able to detect blood volume changes signifying the presence of a hematoma (the most severe case of TBI), as well as a change of the blood oxygenation or degeneration (methemoglobin saturation) within the hematoma. Information on blood oxygenation or information on blood degeneration (methoemoglobin saturation) within the hematoma are extremely important parameters in evaluating and treating a TBI that are currently not routinely available to physicians who are called on to treat TBI events in patients. It is generally understood that all forms of TBI are associated with hemodynamic changes, and such changes may be potentially detected with the system 10 and method of the present disclosure. The system 10 and method of the present disclosure is also expected to find application in addressing other clinical conditions such as cancer and vascular diseases. Virtually any condition where imaging of subsurface anatomical structure of a human or animal is needed may potentially benefit from use of the system 10 and methods described herein.

Manufacturing of Gel-Like IMASC Material

The present disclosure is somewhat related to U.S. Patent Publication 2013/0338504A1, which is incorporated by reference into the present application in full. The present disclosure also discloses two methods to manufacture an optically reflective, gel-like IMASC material (such as gel-like IMASC material 16) suitable for use in a non-contact imaging system. The first involves the addition of a small amount of nanoparticles or other nanostructures to a standard ultrasound imaging gel. Such mixing of the two materials causes a very small change in the gel's acoustic impedance. The light impinging on this gel-like IMASC material will be largely reflected and modulated by the motion of the nanoparticles inside the IMASC.

The second method involves the dispersion of the nanoparticles or other nanostructures in a liquid, for example water, and subsequent addition in the mixture of small amount of agents that alter (increase) the viscosity of the mixture to the desired specifications. The required viscosity of the gel-like IMASC material can be qualitatively described as follows. When a small quantity of the gel-like IMASC material is positioned on the skin, there is no flow of the gel-like IMASC material outside the area where it was positioned. However, the viscosity is low enough so that the surface tension of the gel-like IMASC material is sufficient to create a nearly flat surface. Thus, a portion of a probe light illuminating the gel-like IMASC material can be reflected at the air-IMASC material interface such as via directional and/or specular reflection.

Such nanoparticle infused composite material can be designed to meet specifications required for use as an IMASC material. The ultrasound waves from tissue will propagate to the gel's surface inducing its displacement. The surface tension of the gel makes the surface locally flat, which supports a directional and/or specular reflection component of the light that can subsequently be used to probe the motion of the gel-like IMASC material 16 surface. This surface motion, which arises from the propagating acoustic wave(s), can be detected using a very high sensitivity interferometric approach using instrumentation that is currently commercially available, such as in laser-ultrasonics.

Dispersion of Nanoparticles in Ultrasound Gel

As mentioned above, a suitable gel-like IMASC material substance for use with the present system and method may be constructed by utilizing ultrasound gel containing metal or other type of nanoparticles or nanostructures. The ultrasound gel's main function is to better conduct ultrasonic sound waves arriving at the surface of the body to an external detection device such as a probe. Liquids like water are suitable media, however, water is a rather challenging media to work with because of its volatility and very low viscosity. That is why specific gels have been developed for use in ultrasound imaging. In fact, gels used for ultrasound imaging purposes are typically liquids that contain thickening agents to modify their viscosity, to thus improve the spreadability of the gel on the skin.

There are generally two types of ultrasound gels, and they are typically referred to as "hydrogels" and "lipogels" (oleogels). Lipogels consist of vegetable, synthetic or mineral oils. The main component of hydrogels is water. Hydrogels can be easily removed after the treatment without leaving any residues. Since water-based ultrasound gels consist of more than 90 percent of water, they require adequate preservation which almost exclusively is achieved with highly effective preservatives such as Propylene glycol, Methyl dibromo glutaronitrile, a mixture of methyl isothiazolinone and chloromethyl isothiazolinone, phenoxy ethanol, benzyl alcohol and parabens which are commonly used as preserving agents.

Metal nanoparticles are commercially available and are sold in liquid solutions or as dry powder (see http://nanocomposix.com/products/econix). These nanoparticles in their dry form can be dispersed in a liquid using an ultrasonic liquid processor (see http://www.sonicator.com). Some of these dry nanoparticle powders have various types of coatings which can interfere with, and/or chemically interact with, the gel when mixed.

The research performed in connection with the subject matter of the present disclosure has involved work focusing on not only dispersing the nanoparticles, but also on controlling the viscosity and optical properties of the resulting mixture of gel/nanoparticles to attain the required optical properties that enable use of the resulting mixture as an excellent gel-like IMASC material (i.e., gel-type IMASC material 16). In this regard an effort was made to achieve properties for the gel/nanoparticle mixture that provide the mixture with the ability to create a significant specular reflection component. This in turn allows the detection and quantifying, from the specular reflection component of the optical signals, the strength and spectral characteristics of the acoustic signals that propagate up to the tissue and IMASC surface. The specular reflection component of the optical signals that are modulated by the acoustic signals are received and analyzed by the optical ultrasound detection system 18, by monitoring the motion of the surface of the gel-type IMASC material 16.

Still another important property or trait of the gel-type IMASC material 16 is that the viscosity of the gel-type IMASC material 16 remains within a range that allows the surface to become locally flat after its application on the tissue. In addition, the gel-type IMASC material 16 does not spread, or flow, beyond the area where it is initially applied. It must be noted that regular ultrasound gel has a viscosity that is higher, or borderline, to that required for use with the present system and method.

Still another important property or trait of the gel-type IMASC material 16 is that its acoustic impedance remains similar to that of the tissue. This property strongly depends on the initial impedance of the gel used as a base material for the gel-type IMASC material 16, and also the amount and type of nanoparticles or other particles interacting with the light of the detection system 18 introduced into the base gel. It must be noted that creams containing nanoparticles are freely available to consumers at the present time. Such creams are generally considered to be completely safe, and furthermore are presumed to provide certain health benefits (see for example http://www.silversolutionusa.com). Therefore, the proposed gel-type IMASC material 16 can be manufactured with constituents that pose no health risk to the user or the patient. Once the gel-type IMASC material 16 is synthesized, the nanoparticles will be contained in the base gel and there will be no possibility of inhalation exposure or other type of contamination risk or hazardous exposure.

An array of nanoparticles was tested for mixing with both hydrogels and lipogels. The following will describe two specific types that were tested that led to synthesis of gel-nanoparticle mixtures with the necessary properties discussed above for successful use with the gel-type IMASC material 16.

Mixing was achieved using the Digital Ultrasonic Piezo Dental Scaler. This instrument is suitable for synthetizing small quantities of material in a laboratory environment. A suitable modification is required to scale production of larger quantities but this does not mean that larger and more powerful instruments will be suitable. This approach provides, locally around the moving metal nanoparticles, sufficient energy and mixing ability to disperse the nanoparticles in the gel independent of the nanoparticle and gel specific composition. The energy (amplitude of the vibration) of the Ultrasonic Piezo Dental Scaler needs to be within a certain predetermined range. Use of an energy below the predetermined range can lead to poor mixing. Higher energies lead to excessive heating, which in turn can lead to adverse effects.

Mixing with this method is possible but the stability of the resulting mixture can vary widely depending on the specific base gel and nanoparticle combination. As a result, certain combinations of nanoparticle-gel materials do not lead to a mixture that is suitable as IMASC material. On the other hand, some nanoparticles that do not mix properly with hydrogels can form an excellent combination with lipogels. Overall proper mixing and stability of the mixture depends on the surface chemistry and functionalization of the nanoparticles in combination with the corresponding properties of the host gel. It is well known that the zeta potential (a scientific term for electrokinetic potential) plays a critical role in the stability of colloidal dispersions. For the case of nanoparticles, a high zeta potential will be associated with increased resistance to aggregation. Similar requirements are applicable in our case, where the nanoparticles are dispersed in a high viscosity host material.

In addition, the co-inventors have found that the viscosity of the resulting mixture changes and depends on: 1) the nanoparticle material; 2) the size of the nanoparticles; and 3) the nanoparticle concentration in the gel-nanoparticle mixture. It is also expected that if a coating material is used on the dry nanoparticles, that such coating material can enter the mixture and affect its viscosity and/or resulting zeta potential. A proper termination (functionalization) of the nanoparticles' surface, the nanoparticle concentration, the host material chemistry and viscosity as well as the mixing method are all important aspects that influence the quality and stability of the mixture. This highlights that for synthesizing a suitable IMASC material, all of the parameters discussed above need to be considered and properly controlled.

Specific Case Examples

Two specific case examples will now be presented. The first is the use of 50 nm average diameter dry silver nanoparticles (from nanoComposix) mixed in water based commercially available ultrasound gel. The water based ultrasound gel and the dry nanoparticles were placed in a container. While the Piezo Dental Scaler was on the OFF position, the two materials were initially mixed by stirring. After a nearly uniform appearance of the mixture was achieved, the Piezo Dental Scaler was turned ON. The mixing was thereafter continued for a period of time while samples were taken and placed under the microscope to examine the homogeneity of the mixture. The goal was to mix the two materials until no visible aggregation of nanoparticles was visibly present under 500× magnification of the resulting mixture. The viscosity was reduced from the original of the conventional ultrasound gel and was qualitatively within the range required for IMASC application as described previously. About 10% of the probe light was specularly reflected of the surface while the remaining light was mostly absorbed (depending on the probe light wavelength) by the IMASC material before reaching the tissue. It must be noted that a similar mixture of the water based ultrasound gel and 20 nm average diameter dry silver nanoparticles led to a mixture with lower viscosity that required additional processing (using a thickening agent) in order to meet the qualitative requirements for IMASC material.

The second specific example involved using 20 nm (10-30 nm) average diameter dry $TiO_2$ nanoparticles from SkySpring Nanomaterials Inc. of Houston, Tex. The $TiO_2$ nanoparticles were mixed in a lipogel. The oil based gel and the dry $TiO_2$ nanoparticles were placed in a container. While the Piezo Dental Scaler was on the OFF position, the two materials were mixed. After a nearly uniform appearance via naked eye examination of the mixture was achieved, the Piezo Dental Scaler was turned ON. The mixing was thereafter continued for a period of time of about 20 minutes interrupted by wait times to allow cooling of the mixture at near room temperature. During the wait time, samples were taken and placed under the microscope to examine the homogeneity of the mixture. The goal was to mix the two materials until no visible aggregation of nanoparticles existed while the mixture was viewed under 500× magnification. The mixture led to a material that had the optical properties of the nanoparticles. The viscosity of the mixture was qualitatively within in the range required for IMASC application as described previously. About 10% of the probe light was specularly reflected of the surface while the remaining probe light was diffusively reflected by the IMASC material before reaching the tissue. It is not clear if any percentage of the light was absorbed by the mixture but such absorption would have been very low. The stability of this mixture has been shown to be maintained for months or longer.

The amount of nanoparticles in both case examples discussed above was adjusted so that within the thickness of the IMASC material, once positioned on the skin, only a small percentage of the probe light could penetrate the IMASC material to reach the tissue. The exact values and specification for the transmitted light, and thus the concentration of the nanoparticles, may be determined and selected in accordance with the specific requirements of a given application. In particular, the detection light from the detection system 18 that reaches the tissue after penetrating through the IMASC material can be absorbed, and can generate competing signals to those generated by the ELS laser 12. These parasitic signals must be controlled via either elimination of their origin (no light penetrates the IMASC material) or via electronic means, such as by using a CW detection source that generates CW signals that can be filtered out from the pulsed signals generated by the ELS laser 12 at the target location.

Dispersion of Nanoparticles in Water Followed by Addition of Material to Control Viscosity Water was initially utilized to disperse the nanoparticles using dispersion methods that are well established and available by the nanoparticle manufacturers. As one example, an ultrasonic liquid processor may be used for this purpose. No preservatives were added after and/or during or prior to the dispersion, as the addition of preservatives was considered to be a trivial task. Such preservatives may be included, however, in a production setting for practical implementation of the presently described method for manufacturing of a suitable IMASC material. However, in order to increase the viscosity of the water-nanoparticle solution to attain the required IMASC physical properties, searching was conducted for suitable substances that could be added to a base gel to control the viscosity of the resulting mixture. The co-inventors discovered that commonly used substances in the food industry can increase the viscosity of the solution. Particularly, the co-inventors investigated two specific examples. The first was sold under the name "Instant Pectin" by 2010 Heakthmark, LLC (dba Jarden Home Brand), which is available for retail purchase at some grocery stores. A very small amount of this material (estimated to be about 1 part per 20 parts of the overall solution) was added into the solution after dispersion. Within about 10 minutes, the viscosity of the solution started increasing while the solution was kept at room temperature. The second material is available for retail purchase under the name "Guar Gum", from NOW™ Foods of Bloomingdale, Ill. (also available retail from Amazon.com). Similar results were obtained, although the quality of mixing in the solution was not as good as with the Instant Pectin discussed above. The co-inventors postulate that other substances used in the food, chemical and healthcare industries may also provide similar results in increasing the viscosity using the methods detailed above.

While the system 10 and method of the present disclosure has been described in connection with imaging subsurface tissue of humans, it will be appreciated that the system and method is expected to have utility in a wide range of areas. Such areas include in veterinary medicine, in basic animal research and drug discovery (for pharmacodynamics and pharmacokinetics studies). The system 10 and method of the present invention is especially well suited for those applications where traditional ultrasound is ineffective, such as when attempting to image through the human skull or other bony structures to tissue underneath.

Summary of Considerations and Characteristics Regarding the Gel-Like IMASC Material As a summary of considerations concerning the gel-like IMASC material 16 and its use in the system 10, the following may be observed:

The optical excitation signal generating system 12 may generate pulses of light that have a time duration of less than 1 second.

The optical excitation signal generating system 12 may generate pulses of light that have a time duration from about 0.5 nanoseconds to about 100 nanoseconds.

The optical excitation signal generating system 12 may generate optical frequencies at least at one of: optical frequencies centered around one central frequency; or sequentially at two or more frequency ranges centered around two or more different central frequencies.

The gel-like IMASC material 16 may have a viscosity high enough so that the gel-like IMASC material at least one of: does not flow; or has a minimal flow, outside the area where it is positioned.

The gel-like IMASC material 16 may have a viscosity low enough to create a nearly flat surface upon it application.

The gel-like IMASC material 16 may have a nearly flat surface upon its application on the tissue so at least a portion of an optical signal illuminating the gel-like IMASC material 16 can be directionally or specularly reflected at an air-IMASC material interface to form the reflected signal.

The gel-like IMASC material 16 may be based on either a hydrogel or a lipogel that has an acoustic impedance similar to that of the tissue, and which is supplemented by additional material elements that interact with the optical signal illuminating the gel-like IMASC material 16 to impart the information represented by the acoustic signals into corresponding optical signals.

More than about 5 percent of the optical signal illuminating the gel-like IMASC material 16 may be back-reflected and less than about 95 percent may be transmitted through the gel-like IMASC material 16.

The gel-like IMASC material 16 may allow substantially the entire spectrum of ultrasonic, acoustic or pressure wave signals entering the gel-like IMASC material from the tissue to be converted and analyzed into optical signals.

The material elements in the gel-like IMASC material 16 are embedded in the gel-like IMASC material and enable the conversion of acoustic signals into corresponding optical signals. The material elements are at least one of nearly spherical or non-spherical nanoparticles, and the nanoparticles may be comprised of at least one of: metal nanoparticles, metal oxide nanoparticles, alloy nanoparticles, semiconductor material nanoparticles, dielectric material nanoparticles, nanowires, organic material nanoparticles or other type of nanostructure having at least one dimension about equal or smaller to the wavelength of the optical detection system.

The gel-like IMASC material 16 may be formed by first embedding the nanoparticles into a base gel-like material and subsequently dispersing them within the base gel-like material by applying energy, pressure or forces into the mixture using an at least one of an external source of energy, pressure or other forces.

The gel-like IMASC material 16 may be formed by first embedding the nanoparticles into a base liquid-like material, and subsequently introducing one or more thickening agents to modify the mixture viscosity to a gel-like consistency.

The gel-like IMASC material 16 may be formed by embedding the nanoparticles into a base liquid-like material, and wherein the embedded nanoparticles undergo surface chemistry and functionalization prior to embedding in the base liquid-like material to achieve stability of the gel-like IMASC material and minimize aggregation of the nanoparticles.

While various embodiments have been described, those skilled in the art will recognize modifications or variations which might be made without departing from the present disclosure. The examples illustrate the various embodiments and are not intended to limit the present disclosure. Therefore, the description and claims should be interpreted liberally with only such limitation as is necessary in view of the pertinent prior art.

What is claimed is:

1. A system for non-contact detection and/or imaging and/or monitoring target subsurface tissue of a target, the system comprising:

a housing;

an optical excitation light generating system housed in the housing and forming a first light source for generating an optical excitation signal applied to an outer tissue surface at a first location on the target, which excites the target subsurface tissue to produce acoustic signals which are transmitted back to the outer tissue surface of the target;

first and second gel-like, impedance matching and signal converting (IMASC) material portions which are adapted to be applied to the outer tissue surface at a pair of spaced apart second locations on the target, the IMASC material portions containing material elements embedded therein which are able to influence characteristics of an optical signal impinging and reflected from the IMASC material portions at the pair of spaced apart second locations on the target, in accordance with acoustic signals that have been reflected from the target subsurface tissue, and which propagate into the IMASC material portions at the pair of spaced apart second locations on the target;

an optical heterodyne ultrasound detection system housed in the housing, and including a photodetector and a second light source, the second light source configured to emit at least one optical signal, which is split into a first emitted signal portion and a second emitted signal portion;

the gel-like IMASC material portions operating to receive the first and second emitted signal portions at the second locations and to reflect back a pair of first reflected signal portions, where each one of the pair of first reflected signal portions is modified by the gel-like IMASC material in relation to the acoustic signals reaching the IMASC material at the second locations;

the optical heterodyne ultrasound detection system further including being housed adjacent the optical excitation light generating system within the housing to enable the transmission of the optical excitation signal, the transmission of the first and second emitted signal portions, and the reception of the pair of first reflected signal portions, all from a single location represented by the housing;

the photodetector being configured and positioned to receive both ones of the pair of first reflected signal portions for processing by the optical heterodyne detection system, the processing including analyzing resulting differences between the pair of first reflected signal portions and a second reflected reference signal portion, to generate electrical signals that relate to optical and physical properties of the subsurface target tissue; and wherein the IMASC material portions each have a viscosity high enough so that each one of the IMASC material portions at least one of:
   does not flow; or
   has a minimal flow, outside the area where it is positioned; and
wherein the IMASC material portions are each based on either a hydrogel or a lipogel that has an acoustic impedance similar to that of the tissue that is supplemented by additional material elements that interact with the first and second emitted signal portions illuminating the IMASC material portions to impart the information represented by the acoustic signals into corresponding optical signals; and
wherein the material elements embedded in the IMASC material portions have at least one spatial dimension about the same or smaller than the wavelength of the optical heterodyne ultrasound detection system.

2. The system of claim 1, wherein the optical excitation light generating system generates pulses of light that have a time duration of less than 1 second.

3. The system of claim 1, wherein the optical excitation light generating system generates pulses of light that have a time duration from about 0.5 nanoseconds to about 100 nanoseconds.

4. The system of claim 1, wherein the optical excitation light generating system generates optical frequencies at least at one of:
   optical frequencies centered around one central frequency; or
   sequentially at two or more frequency ranges centered around two or more different central frequencies.

5. The system of claim 1, wherein the IMASC material portions each have a nearly flat surface upon its application on the tissue so at least a portion of the first and second emitted signal portions illuminating the IMASC material portions can be directionally or specularly reflected at air-IMASC material portion interface areas to form the pair of first reflected signal portions.

6. The system of claim 1, wherein more than about 5 percent of the first and second emitted signal portions illuminating the IMASC material portions is back-reflected and less than about 95 percent is transmitted through the IMASC material portions.

7. The system of claim 1, wherein the IMASC material portions allow substantially the entire spectrum of ultrasonic, acoustic or pressure wave signals entering the IMASC material portions from the tissue to be converted and analyzed into optical signals.

8. The system of claim 1, wherein the material elements enable the conversion of acoustic signals into corresponding optical signals, and wherein the material elements are at least one of nearly spherical or non-spherical nanoparticles, and wherein the nanoparticles are comprised of at least one of:
   metal nanoparticles,
   metal oxide nanoparticles,
   alloy nanoparticles,
   semiconductor material nanoparticles,
   dielectric material nanoparticles,
   nanowires, or
   organic material nanoparticles.

9. The system of claim 8, wherein the IMASC material portions are formed by first embedding the nanoparticles into a base gel-like material and subsequently dispersed within the base gel-like material by applying energy, pressure or forces into the mixture using an at least one of an external source of energy, pressure or other forces.

10. The system of claim 8, wherein the IMASC material portions are formed by first embedding the nanoparticles into a base liquid-like material, and subsequently introducing one or more thickening agents to modify the mixture viscosity to a gel-like consistency.

11. The system of claim 8, wherein the IMASC material portions are formed by embedding the material elements into a base material, and wherein the embedded material elements undergo surface chemistry and functionalization prior to embedding in the base material to achieve stability of the IMASC material and minimize aggregation of the material elements.

12. A system for non-contact detection and/or imaging and/or monitoring a target having subsurface tissue, the system comprising:
   a housing;
   an optical excitation light generating system forming a first light source and housed within the housing for generating optical excitation signals applied to an outer tissue surface at a first location on the target, which excite the target subsurface tissue to produce acoustic signals which are transmitted back to the outer tissue surface of the target;
   first and second gel-like, impedance matching and signal converting (IMASC) material portions which are adapted to be applied to the outer tissue surface at a pair of spaced apart second locations on the outer tissue surface of the target different from the first location, the IMASC material portions each containing material elements therein which are able to influence characteristics of an optical signal impinging and being reflected from the IMASC material portions, in accordance with acoustic signals that have been reflected from the target subsurface tissue, and which propagate into the IMASC material; and
   an optical heterodyne ultrasound detection system housed in the housing and including a detector and at least one second light source, both housed in the housing, the at least one second light source configured to generate emitted optical signals at the pair of spaced apart second locations to impinge the gel-like IMASC material portions, which operate to receive the emitted optical signals and to reflect back reflected optical signals;
   the optical heterodyne ultrasound detection system also configured to direct a reference beam at a reference location different from the pair of second locations of the gel-like IMASC material portions, to produce a reflected reference signal portion, and where the reflected optical signals are modified by the gel-like IMASC material portions in relation to the acoustic signals; and
   the optical heterodyne ultrasound detection system further including the detector housed in the housing adjacent the optical excitation light generating system, for receiving both of the reflected optical signals and the reflected reference signal portion, and configured to provide signals to the optical heterodyne ultrasound detection system for processing differences between the reflected optical signals and the reflected reference signal portion to generate electrical signals that relate to optical and physical properties of the subsurface target tissue;
   the optical excitation light generating system and the optical heterodyne ultrasound detection system enabling the transmission of the optical excitation signal, the transmission of the emitted optical signals and the reception of the reflected optical signals, all from a single location represented by the housing;

wherein the IMASC material portions each have a viscosity high enough so that each of the IMASC material portions at least one of:

does not flow; or has a minimal flow, outside the area where it is positioned;

wherein the material elements are embedded in each of the IMASC material portions and enable the conversion of acoustic signals into corresponding optical signals; and wherein more than about 5 percent of the optical signal illuminating the IMASC material portions is back-reflected and less than about 95 percent is transmitted through the IMASC material portions; and wherein the material elements are at least one of nearly spherical or non-spherical nanoparticles, and wherein the nanoparticles are comprised of at least one of:

metal nanoparticles, metal oxide nanoparticles, alloy nanoparticles, semiconductor material nanoparticles, dielectric material nanoparticles, nanowires, or organic material nanoparticles; and wherein each of the gel-like IMASC material portions has a viscosity low enough to create a nearly flat surface.

* * * * *